(12) United States Patent
Akutsu et al.

(10) Patent No.: US 9,063,104 B2
(45) Date of Patent: Jun. 23, 2015

(54) AUTOMATIC ANALYZER

(75) Inventors: Masashi Akutsu, Hitachinaka (JP);
Shigeki Matsubara, Hitachinaka (JP);
Yoshimitsu Takagi, Hitachinaka (JP);
Hitoshi Tokieda, Hitachinaka (JP)

(73) Assignee: Hitachi High-Technologies Corporation, Tokyo (JP)

(*) Notice: Subject to any disclaimer, the term of this patent is extended or adjusted under 35 U.S.C. 154(b) by 240 days.

(21) Appl. No.: 13/141,760

(22) PCT Filed: Dec. 4, 2009

(86) PCT No.: PCT/JP2009/006612
§ 371 (c)(1),
(2), (4) Date: Jun. 23, 2011

(87) PCT Pub. No.: WO2010/073502
PCT Pub. Date: Jul. 1, 2010

(65) Prior Publication Data
US 2011/0256022 A1    Oct. 20, 2011

(30) Foreign Application Priority Data

Dec. 25, 2008  (JP) ................. 2008-328998

(51) Int. Cl.
*G01N 35/04* (2006.01)
*G01N 35/00* (2006.01)

(52) U.S. Cl.
CPC ...... *G01N 35/04* (2013.01); *G01N 2035/00891* (2013.01); *G01N 2035/0462* (2013.01); *G01N 35/00603* (2013.01); *G01N 2035/0415* (2013.01)

(58) Field of Classification Search
USPC ............................................... 422/65; 436/47
See application file for complete search history.

(56) References Cited

U.S. PATENT DOCUMENTS 5,232,081 A * 8/1993 Kanamori ............... 198/465.2
6,117,392 A * 9/2000 Hanawa et al. ............... 422/65

(Continued)

FOREIGN PATENT DOCUMENTS

JP          03-183957 A    8/1991
JP          10-090276 A    4/1998

(Continued)

*Primary Examiner* — Jill Warden
*Assistant Examiner* — Benjamin Whatley
(74) *Attorney, Agent, or Firm* — Miles & Stockbridge P.C.

(57) ABSTRACT

An automatic analyzer is provided that can promptly process a request for additional test items for a sample being analyzed or an error that has occurred in the sample. The automatic analyzer can output measurements of a sample analyzed, determine whether or not re-analyzing is necessary, and perform the re-analyzing. The automatic analyzer includes a buffer area for standby until analysis is completed and measurements are outputted. Each of analysis units includes a pair of buffer units that can randomly access the buffer area. The automatic analyzer further includes a position disposed near the buffer area, at which a sample can be unloaded and reloaded. A rack that stands by within the buffer area can be unloaded onto the unloading position by a command to unload issued by an operator. Subsequent reloading of the sample allows samples other than the sample in question to be analyzed continuously.

18 Claims, 5 Drawing Sheets

(56) References Cited

U.S. PATENT DOCUMENTS

| | | | |
|---|---|---|---|
| 6,290,907 B1 * | 9/2001 | Takahashi et al. | 422/65 |
| 6,520,313 B1 * | 2/2003 | Kaarakainen et al. | 198/369.5 |
| 2003/0235514 A1 * | 12/2003 | Nogawa et al. | 422/65 |
| 2004/0186360 A1 * | 9/2004 | Suzuki et al. | 600/310 |
| 2006/0177346 A1 * | 8/2006 | Veiner | 422/65 |
| 2008/0069730 A1 * | 3/2008 | Itoh | 422/65 |
| 2008/0271546 A1 * | 11/2008 | Miller et al. | 73/863.92 |
| 2008/0286162 A1 * | 11/2008 | Onizawa et al. | 422/104 |
| 2009/0162247 A1 * | 6/2009 | Tokieda et al. | 422/65 |
| 2010/0010746 A1 * | 1/2010 | Ariyoshi et al. | 702/19 |

FOREIGN PATENT DOCUMENTS

| | | |
|---|---|---|
| JP | 2000-105246 A | 4/2000 |
| JP | 2003-083991 A | 3/2003 |
| JP | 2004-028588 A | 1/2004 |
| JP | 2009-150859 A | 7/2009 |

* cited by examiner

AUTOMATIC ANALYZER

TECHNICAL FIELD

The present invention relates in general to automatic analyzers making quantitative and qualitative analysis of biological samples such as blood and urine and, more particularly, to an automatic analyzer having a transport system for transporting a sample vessel to an analyzer.

BACKGROUND ART

Automatic analyzers automatically make quantitative and qualitative analysis of biological samples such as blood and urine. Such automatic analyzers are in widespread use particularly in large hospitals and clinical laboratory centers which are required to process a large number of patient samples to be analyzed within a short time. The automatic analyzers have therefore been developed in large varieties covering from large, medium, to small sizes according to their processing capacities. In particular, some large-sized analyzer systems analyze large numbers of samples to be analyzed. Such a large-sized analyzer system incorporates a transfer line (transfer unit), via which a plurality of sample vessels, each of the sample vessels containing a sample to be analyzed, held in a holder called a sample rack is transported to a plurality of analyzers, to thereby automatically perform processes of up to an output of an analysis result when a laboratory technician has only to load the rack at a sample rack loading port.

In this case, the sample rack loaded at the sample rack loading port is transported by a belt conveyor-like transport line and a bar code reader disposed on the line recognizing a rack type and a sample for analysis during transport of the rack. An example of such an automatic analyzer system is disclosed in Patent Document 1.

Patent document 1 discloses a system including one transfer means for loading a rack into the analysis unit and the other transfer means for unloading the rack from the analysis unit, the system including an identification means arranged at the upstream side of the analysis unit. The identification means identifies a requested test item for a sample to thereby determine which analysis unit should be assigned for analysis and to instruct the analyzer module in question to receive the rack therein.

In patent document 2, each analysis unit includes a buffer on which racks or the like waiting are stored.

PRIOR ART DOCUMENTS

Patent Documents

[Patent Document 1]
  Japanese Patent Application No. 2002-180741
[Patent Document 2]
  Japanese Patent Application No. 2007-331312

SUMMARY OF THE INVENTION

Problem to be Solved by the Invention

Generally, one piece of testing equipment cannot cover all test items. A plurality of automatic analyzers is therefore installed in a hospital laboratory.

During a sample test, a test result obtained for one test item may bring about an urgent requirement for testing of another test item. In particular, the test result of the additional test item must be outputted promptly for a patient being operated or one brought in for emergency care.

Under these circumstances, if samples are stagnant within an automatic analyzer for reasons of, for example, a need for retesting, lack of means of unloading samples from the analyzer disables testing of the another test item that is required urgently.

In the automatic analyzer disclosed in patent document 1 described above, a path for transporting a rack is determined before the rack is transported to the analysis unit. When analysis using a plurality of analysis units is necessary, therefore, the racks are transported to an upstream side thereof first. When a large number of samples are to be analyzed at the upstream side, the rack transport path is congested, so that a sample that suffices to be analyzed only at a downstream side cannot overtake the former samples.

The automatic analyzer disclosed in patent document 2 described above incorporates a buffer for each analyzer module, offering random accessibility. However, to enable prompt determination of the additional item, which is the problem to be solved by the present invention, the racks need to be unloaded temporarily to a storage section.

Means for Solving the Problem

An automatic analyzer has functions of outputting measurements of a sample analyzed, determining whether or not re-analyzing is necessary, and performing the re-analyzing. To achieve this function, the automatic analyzer includes a buffer area for standby until analysis is completed and measurements are outputted. Each of the analysis units includes a pair of buffer units that can randomly access the buffer area. The automatic analyzer further includes a position located near the buffer area, at which a sample can be unloaded and reloaded. A rack that is mounted with the sample in question and that stands by within the buffer area is unloaded onto the unloading position by a command to unload issued by an operator operating an operation section.

Operations required for the sample are performed from above the unloaded rack. Subsequent reloading of the sample allows samples other than the sample in question to be analyzed continuously.

Effect of the Invention

In accordance with the present invention, the automatic analyzer operating by using the rack can achieve temporary unloading of a sample being analyzed and, as a result, can promptly perform analysis of the sample in question for additional test items.

MODE FOR CARRYING OUT THE INVENTION

One embodiment of the present invention will be described below.

Figure 1:
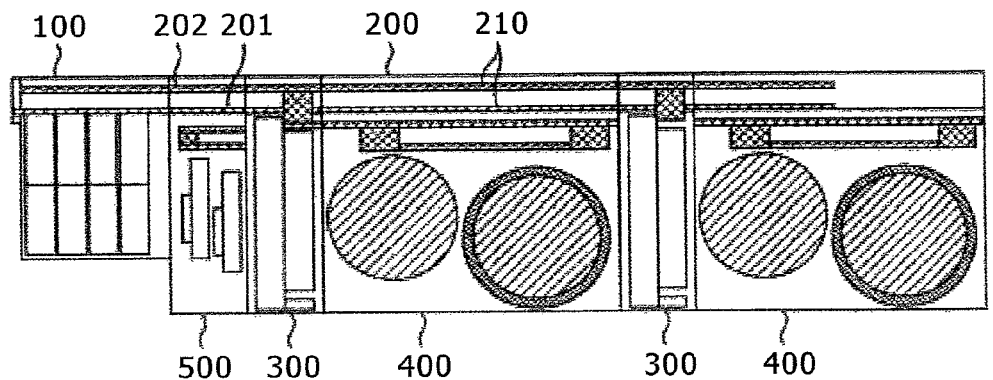
FIG. 1 is a configuration diagram showing an automatic analyzer according to one embodiment of the present invention.

FIG. 1 is a plan view showing an automatic analyzer according to an embodiment of the present invention. FIG. 1 shows, as an example, a system that includes a sampler unit 100, a rack transport unit 200, a buffer unit 300, an analyzer module 400, and an analyzer module 500. The sampler unit 100 loads and stores a sample rack. The rack transport unit 200 transports the sample rack between the sampler unit and each of the analyzer modules. The buffer unit 300 transfers the sample rack with the rack transport unit 200 and temporarily puts the sample rack in a standby state. The analyzer module 400 is disposed on the right of the buffer unit 300. The analyzer module 500 is disposed on the left of the buffer unit 300.

Each of these system components and operation of the entire system will be described below.

Figure 2:
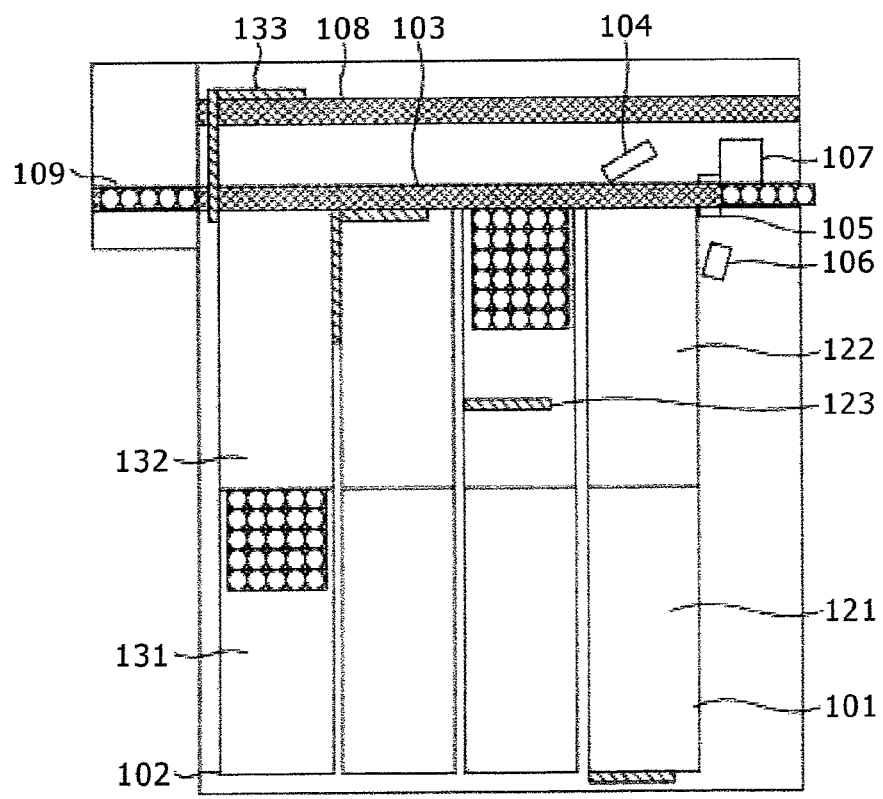
FIG. 2 is a configuration diagram showing a sampler unit according to one embodiment of the present invention.

FIG. 2 shows the configuration of the sampler unit 100.

The sampler unit 100 includes a loading section 101, a storing section 102, a loading rack moving unit 103, a rack ID identifying unit 104, a sample vessel height detecting unit 105, a sample ID identifying unit 106, a sample rotating unit 107, a storing rack moving unit 108, and an emergency sample loading section 109. The loading section 101 loads the sample rack into the system. The storing section 102 unloads the sample rack from the system. The loading rack moving unit 103 transports the sample rack from the loading section onto the rack transport unit 200. The rack ID identifying unit 104 identifies an ID of each sample rack. The sample vessel height detecting unit 105 determines whether or not a sample vessel is disposed in the sample rack and detects a height of the sample vessel. The sample ID identifying unit 106 identifies a sample ID affixed to the sample vessel disposed in the sample rack. The sample rotating unit 107 rotates the sample vessel when the sample ID affixed to the sample vessel disposed in the sample rack is to be identified. The storing rack moving unit 108 moves the rack from the rack transport unit 200 onto the storing section 102. The emergency sample loading section 109 loads an emergency sample rack into the system.

The loading section 101 includes a loading tray disposing section 121, a loading buffer section 122, and a loading lever 123. The loading tray disposing section 121 has a sample rack tray disposed therein, the sample rack tray having a plurality of sample racks disposed therein and being portable. The loading buffer section 122 is disposed between the tray disposing section and the loading rack moving unit 103. In addition, the loading lever 123 transports the sample rack in a Y-direction.

When the sample rack tray is disposed in the loading tray disposing section 121, the loading lever 123 is moved in a positive Y-axis direction. The sample rack is thereby transported via the loading buffer section 122 onto the loading rack moving unit 103. After the loading buffer section 122 runs out of racks, the loading lever 123 moves in a negative Y-axis direction and waits until the next sample rack tray is disposed.

The sample rack tray is removable when all sample racks disposed therein are moved to the loading buffer section 122, so that another new sample rack tray may be disposed.

The system according to the embodiment of the present invention has two sample loading sections. When one of the two sample loading sections completes feeding the sample rack and runs out of racks, the other one starts feeding the sample rack. In accordance with the embodiment of the present invention, there are two sample loading sections. Two or more sample loading sections may be disposed, being configured to perform similar processes sequentially.

The loading rack moving unit 103 moves the rack moved from the loading section onto the rack ID identifying unit 104, at which the rack ID is read. The rack is then moved onto the sample vessel height detecting unit 105.

The sample vessel height detecting unit determines whether or not the sample vessel is disposed in a corresponding position in the sample rack and detects the height of the sample vessel.

The sample rack is thereafter moved to a sample ID reading position and the sample ID is read by the sample ID identifying unit 106.

A bar code is typically used for the sample ID. The sample vessel may, for example, be a cup, a test tube, or a cup placed on a test tube. The bar code as the sample ID is usually affixed to only the test tube for its size requirements for carrying a necessary amount of information. Based on the abovementioned rack ID identification information and sample vessel height information, processing is performed for reading the sample ID and determining the necessity of rotating the sample vessel.

Based on the above-referenced information on the rack ID and sample ID, processing required for the sample rack is determined and a transport destination where the sample rack is to be transported, i.e., the analyzer modules 400 and 500 are selected.

After the transport destination for the sample rack is determined, the loading rack moving unit 103 moves the sample rack onto the rack transport unit 200.

The emergency sample rack is loaded into the sampler unit 100 from the emergency sample loading section 109. The rack loaded from the emergency sample loading section 109 is transported by the loading rack moving unit 103 and subjected to a similar process as that for the rack from the above-mentioned loading section 101 before being moved onto the rack transport unit 200.

The rack that has undergone the necessary processes in each of the analyzer modules 400, 500 is moved to the storing section 102 by the storing rack moving unit 108.

The storing section 102 includes a storing tray disposing section 131, a storing buffer section 132, and a storing lever 133. The storing tray disposing section 131 has a sample rack tray disposed therein, the sample rack tray having a plurality of sample racks disposed therein and being portable, as same as the loading section 101. The storing buffer section 132 is disposed between the storing tray disposing section 131 and the loading rack moving unit 103. In addition, the storing lever 133 moves the storing rack.

The sample rack transported to a point in front of the storing section 102 by the storing rack moving unit 108 is moved by the storing lever 133 to the storing tray on the storing buffer section 132 or the storing tray disposing section 131.

The rack transport unit 200 shown in FIG. 1 includes two rack transport lanes of a feed lane 201 and a return lane 202. The feed lane 201 transports the sample rack from the sampler unit 100 onto each of the analyzer modules 400, 500. The return lane 202 transports the sample rack from each of the analyzer modules 400, 500 to the sampler unit 100.

A belt mechanism 210 uses a conveyor belt to transport, in the feed lane 201 and the return lane 202, the sample rack between the sampler unit 100 and each of the analyzer modules 400, 500. In accordance with the embodiment of the present invention, the conveyor belt includes one feed lane and one return lane. To enhance promptness of processing, the conveyor belt may be provided with a plurality of feed lanes and return lanes for achieving the same effect.

Figure 3:
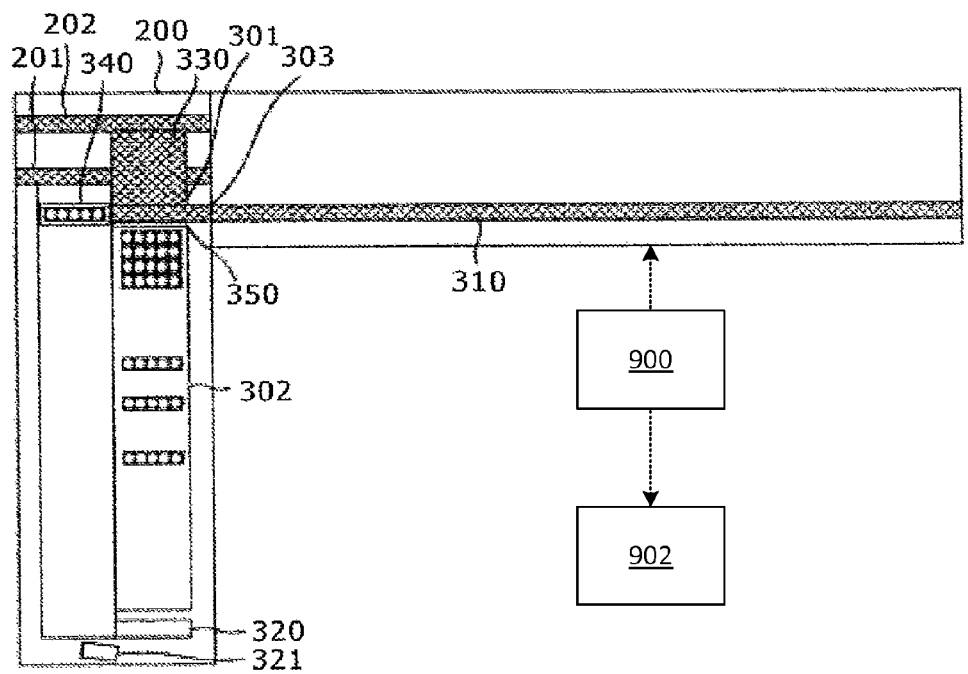
FIG. 3 is a configuration diagram showing a buffer unit according to one embodiment of the present invention.
Figure 4:
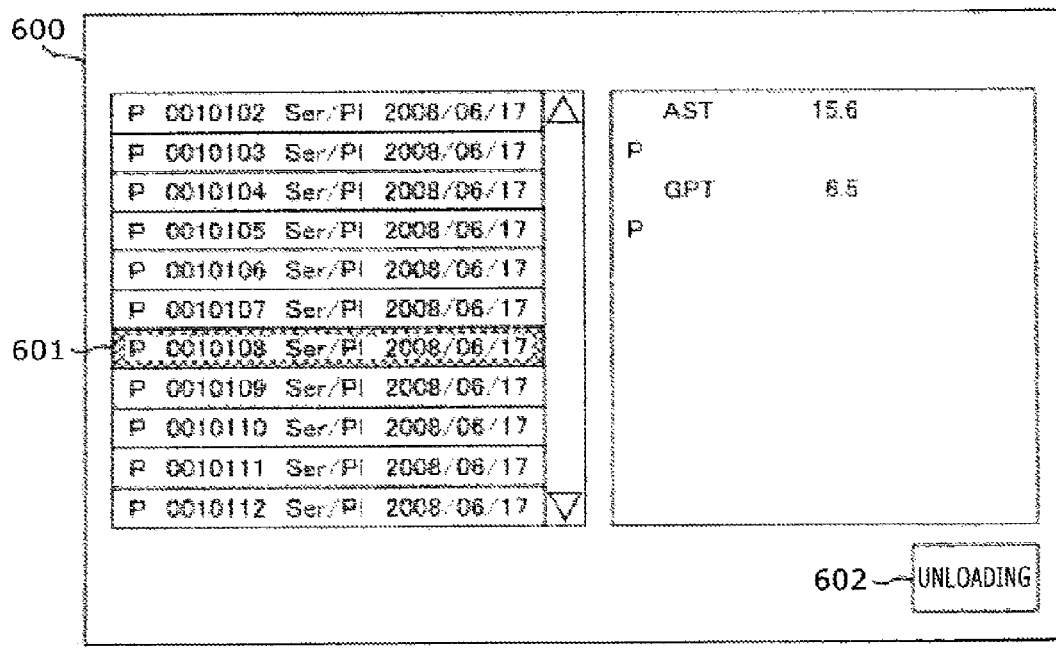
FIG. 4 is an operation screen to be used for issuing a command to unload a sample.
Figure 5:
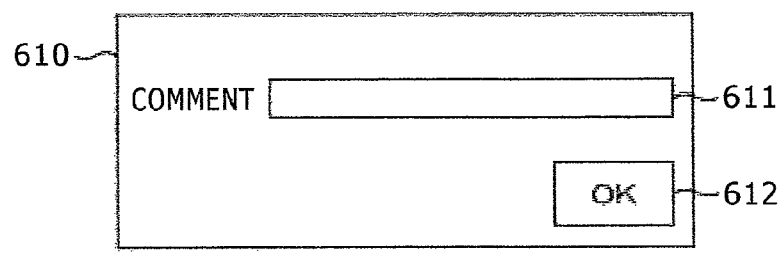
FIG. 5 is an operation screen on which to input comment information to be registered when a command is issued to unload a sample.
Figure 6:
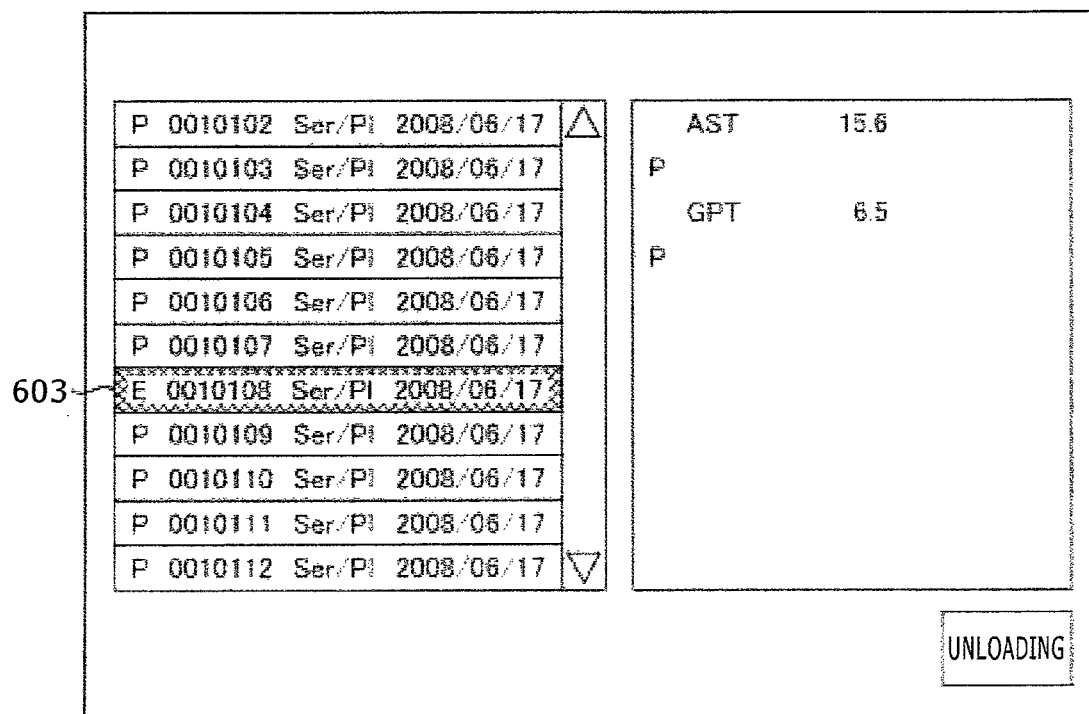
FIG. 6 is an operation screen which indicates that a sample error has occurred and on which to issue a command to unload a sample.

FIG. 3 shows the configuration of the buffer unit 300.

The buffer unit 300 includes a rack entry/exit standby section 301, a buffer section 302, a module entry/exit standby position 303, a rack transport section 310, a one-rack loading/unloading section 320, an ID reading section 321, a rack transfer mechanism 330, a rack moving mechanism 340, and a rack unloading mechanism 350.

The rack entry/exit standby section 301 has a space that allows one rack to be in a standby state. The rack entry/exit standby section 301 is positioned where the sample rack from the rack transport unit 200 is to be transferred onto the buffer unit 300 where the sample rack to be unloaded from the buffer unit 300 to the rack transport unit 200 is to be put in a standby state.

The buffer section 302 includes a plurality of independent slots to make the sample rack in a standby state temporarily.

The module entry/exit standby position 303 has a space that allows one rack to be in a standby state. The module entry/exit standby position 303 is positioned where the sample rack from the buffer unit 300 is to be carried out onto the analyzer module 400 and where the sample rack that has undergone an analysis by the analyzer module 400 is to be carried back in the buffer unit 300.

The rack transport section 310 transports the sample rack between the module entry/exit standby position 303 and the analyzer module 400.

The one-rack loading/unloading section 320 serves as a rack loading/unloading section for performing sample rack processing at the analyzer modules 400, 500 without using the rack transport unit 200.

The rack transfer mechanism 330 transfers the sample rack between the rack entry/exit standby section 301 and the feed lane 201 and the return lane 202 of the above-described rack transport unit 200 bi-directionally.

The rack moving mechanism 340 transfers the sample rack among the rack entry/exit standby section 301, the buffer section 302, the module entry/exit standby position 303, and the one-rack loading/unloading section 320.

The rack unloading mechanism 350 has a function of feeding the sample rack on the module entry/exit standby position 303 onto the rack transport section 310. The rack unloading mechanism 350 also has a function of feeding the rack onto the analysis unit 500 disposed on the left side of the buffer unit 300.

The analysis units 400, 500 load the sample rack from the buffer unit 300, perform analysis of an item requested for the sample, and unload the sample rack onto the buffer unit 300.

Figure 7:
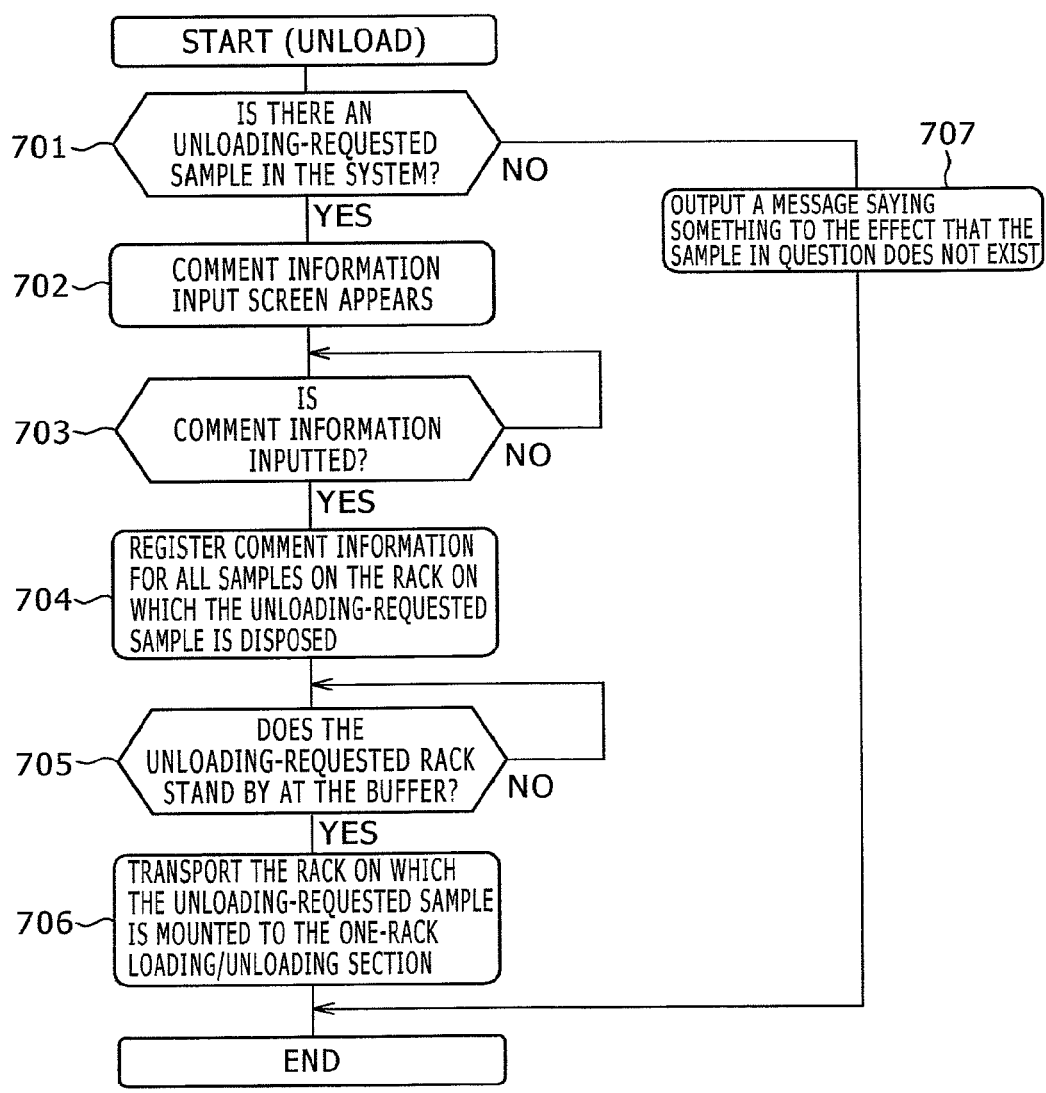
FIG. 7 is a flowchart showing processes for unloading a sample.

A sample unloading process flow will be described with reference to FIG. 7.

In automatic analyzers, processes for analyzing a sample include suction of the sample, addition of reagents, and wait for incubation time, it taking several minutes before measurements are outputted. In addition, the measurements of the sample are reviewed to determine whether or not an abnormality exists and, if the sample is not normal, re-analysis processes are performed.

Consequently, the sample rack stands by at a predetermined standby position after a sample dispensing process is completed. In accordance with the embodiment of the present invention, the sample rack stands by on the buffer section 302.

When the reaction time elapses and the measurements are fixed, a decision is made as to whether or not a re-analysis is necessary. If a decision that a re-analysis is necessary is made, the sample rack is transported again to the analyzer modules 400, 500 for analyzing processes. On the other hand, if a decision that no re-analysis is necessary is made, the sample rack is transported to the storing section 102 via the rack transport unit 200.

Reaction time for analysis items required in a common colorimetric method is three to ten minutes. The sample rack that contains a sample in a state of waiting for a re-analysis stands by on the buffer section 302. If an analysis request for an urgent test item is made additionally, an operator makes a choice 601 for a sample to unload on an unloading sample selection screen 600 of an operation screen of an instruction means 900 and presses an unloading command key 602.

When the unloading command key 602 is pressed, a search process 701 is performed to determine whether or not an unloading-requested sample for which unloading is requested stands by in the system. If no samples for which a command is issued to unload exist in the system, it follows that the sample has already been transported onto the storing section 102, so that a message 707 that says something to the effect that the sample in question does not exist is outputted.

If the unloading-requested sample exists in the system, a comment information input screen output step 702 is performed, so that an unloading sample comment input screen 610 is displayed.

A plurality of samples can be disposed on the sample rack. However, only one of the samples needs to be unloaded in many cases. In such cases, to make it clear that a process for unloading a specific sample temporarily interrupts an otherwise normally run process, comment information 611 is inputted in a comment information registration step 704 to thereby add the comment information 611 by recording means 902 with respect to all samples on the sample rack.

Next, it is determined in an unloading rack search step 705 whether or not the unloading-requested sample stands by at the buffer section 302. If the rack in question does not stand by at the buffer section 302, the condition is continued.

If the rack in question stands by at the buffer section 302, the rack in question on the buffer section 302 is moved, in an unloading transport process step 706, to the one-rack loading/unloading section 320.

The operator can remove the rack moved and extract the sample from the rack.

Figure 8:
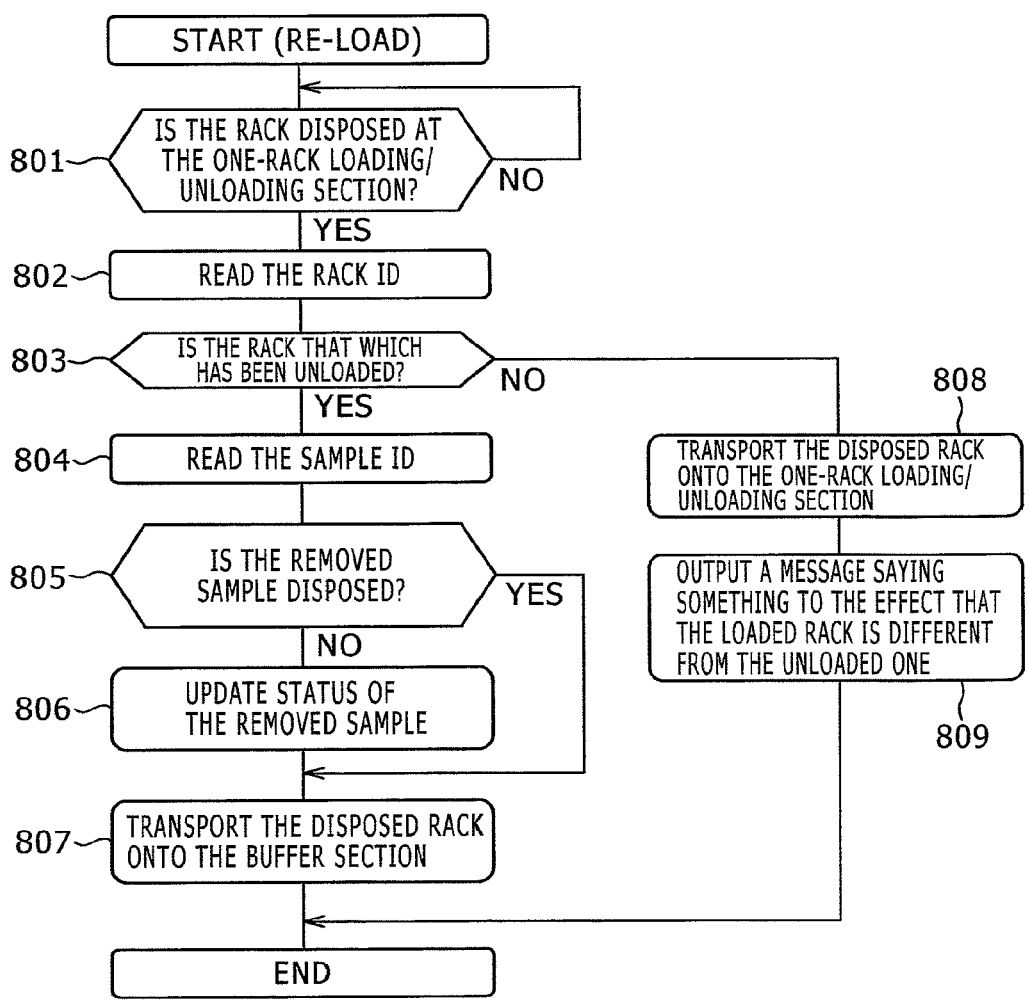
FIG. 8 is a flowchart showing processes for reloading a sample that has been unloaded.

A sample reloading process flow will be described with reference to FIG. 8.

The operator disposes a sample rack in the one-rack loading/unloading section 320 again.

At a rack disposing detection step 801, it is recognized that the rack is set. In a rack ID reading step 802, the rack is moved to the ID reading section 321, the rack ID being read. In an unloaded-rack determination step 803, it is determined if the loaded rack is the rack that has been unloaded by the unloading process described above.

If the loaded rack is different from the unloaded rack, the set rack is moved to the one-rack loading/unloading section 320 and the process is terminated at a step 809 for outputting a message that the loaded rack is different from the unloaded rack.

If the loaded rack is the same as the unloaded rack, the sample ID is read at step 804 and it is determined in step 805 if the same sample is removed through the unloading process.

If the sample to be removed is disposed, the process is being continued.

If the sample to be removed is not disposed, it means that the sample to be removed has been removed. Then, in step 806, a processing status of the same sample is updated, so that the same sample is not to be re-analyzed thereafter.

When processing of all of samples on the disposed rack is completed, the disposed rack is transported to the buffer section 302, returning to the flow of analyzing processes performed so far.

A timeout period is set for re-disposing of the sample.

This is because, if an unloaded sample is re-disposed after all measurements of the sample on the rack are outputted, the processing status of the sample is changed from that of being unloaded to that of measurement completed.

If the timeout period is yet to elapse, specifically, if the processing status of the sample is that of being unloaded, the analysis can continue through the abovementioned re-disposing. If the timeout period elapses, specifically, if the processing status of the sample is changed to that of measurement completed, the disposed rack is moved to the one-rack loading/unloading section 320 and the process is terminated with a message that a rack disposing is disabled.

Referring to FIG. 1, the system according to the embodiment of the present invention has a plurality of buffer units 300 and, therefore, a plurality of one-rack loading/unloading sections 320. For example, the buffer units 300 are numbered sequentially in numerical order from the one adjacent the sampler unit 100. Then, it is permitted that a rack is unloaded from a first one-rack loading/unloading section 320 and a rack is disposed at a second one-rack loading/unloading section 320.

In this case, in step 803, the status of the sample unloaded is controlled and the status of the sample being unloaded is recognized, so that the sample can be stored in the buffer section 302 of a second buffer unit 300.

In general, when a large number of samples are continuously analyzed, in rare cases some samples may be short of a required dispensing volume or others may clog due to a suspended substance (fibrin) contained therein.

The prior art analyzer was unable to continue analyzing such a sample and had nothing but to cancel all including test items for a sample short of a required dispensing volume. Moreover, the rack including the sample also includes other samples. The rack is unloaded only after analyzing of these samples is completed. As a result, it took a tremendous amount of time before the above sample could be subjected to re-analysis.

According to the automatic analyzer of the present invention, when the above-mentioned sample is loaded, a sample error status 603 (identified by "E" according to the embodiment of the present invention) is displayed. When the samples is selected and the unloading key 602 is depressed, the sample error status 603 is transited to the status of unloading operation continuous condition, thus enabling unloading.

With respect to the sample recognized as an abnormal sample, error, if there is a short supply of sample volume, an additional amount of sample is added, and if there is a suspended substance, the substance is removed before re-disposing the sample, so that the temporarily interrupted analyzing process can continue. In addition, it is possible to perform the measurement which is cancelled in case of a prior technique.

Additionally, a single automatic analyzer can rarely test all of necessary items in actual laboratories. Plural automatic analyzers are generally installed in a laboratory and sample may be tested one by one in order.

Under these circumstances, there may be a case in which a new request may be made to test additional items during the sample measuring operation.

In such cases, according to the automatic analyzer of the present embodiment, the priority of the newly added test item is determined. If it is determined that the test item has a higher priority and the currently analyzing automatic analyzer cannot analyze the test item, the status of measuring is temporarily interrupted and the sample may be unloaded onto the one-rack loading/unloading section 320.

The unloaded sample is removed and then disposed in another automatic analyzer, so that the newly requested test item can be analyzed. If the sample volume is expected to be in short supply even if it is determined that the additional test item can be analyzed in the automatic analyzer that is currently analyzing, the same unloading process is performed, so that an additional amount of sample can be added and reloaded.

DESCRIPTION OF REFERENCE NUMERALS

100: sampler unit
101: loading section
102: storing section
103: loading rack moving unit
104: rack ID identifying unit
105: sample vessel height detecting unit
106: sample ID identifying unit
107: sample rotating unit
108: storing rack moving unit
109: emergency sample loading section
121: loading tray disposing section
122: loading buffer section
123: loading lever
131: storing tray disposing section
132: storing buffer section
133: storing lever
200: rack transport unit
201: feed lane
202: return lane
210: belt mechanism
300: buffer unit
301: rack entry/exit standby section
302: buffer section
303: module entry/exit standby position
310: rack transport section
320: one-rack loading/unloading section
321: ID reading section
330: rack transfer mechanism
340: rack moving mechanism
350: rack unloading mechanism
400, 500: analyzer module
600: unloading sample selection screen
601: unloading sample selected status
602: unloading command key
603: sample error status
610: unloading sample comment input screen
611: unloading sample comment input area
612: unloading sample comment registration key
701, 805: unloading sample search step
702: comment information input screen display step
703: comment information input determination step
704: comment information registration step
705: unloading rack search step
706, 808: unloading transport process step 707: no-applicable-sample message output step
801: rack disposing detecting step
802: rack ID reading step
803: unloaded-rack determination step
804: sample ID reading step
806: unloaded-rack status update step
807: buffer section transport process step
809: non-unloaded-rack message output step

The invention claimed is:

1. An automatic analyzer comprising:
an analysis unit for analyzing a sample;
a rack transport unit for transporting a sample rack, which holds a plurality of samples in respective sample vessels, to the analysis unit;
a rack loading section for supplying the sample rack to the rack transport unit;
a rack collecting section for collecting the sample rack from the rack transport unit;
a buffer unit for holding the sample rack in a standby position;
wherein the buffer unit is constructed such that the sample rack can be transported from the standby position to the analysis unit without using the rack transport unit; and
an instruction means for controlling the automatic analyzer to unload the sample rack, wherein the instruction means controls the automatic analyzer to move the sample rack to a rack unloading position in the buffer unit when instructed to unload the sample in one of the sample vessels of the sample rack,
the sample rack can be unloaded from the rack unloading position to an exterior of the automatic analyzer without passing through the rack transport unit,
the instruction means is configured to perform a search to determine if the sample instructed to unload is in the automatic analyzer, and
the instruction means is further configured to:
when it is determined that the sample instructed to unload is not in the automatic analyzer, display on a screen that the sample instructed to unload is not in the automatic analyzer, and
when it is determined that the sample instructed to unload is in the automatic analyzer, display on the screen an input field for a comment.

2. The automatic analyzer according to claim 1, wherein the buffer unit is constructed such that the sample rack unloaded from the automatic analyzer can be reloaded into the automatic analyzer at the rack disposing position so as to bypass the rack transport unit.

3. The automatic analyzer according to claim 2, wherein the buffer unit includes an ID reading section for identifying sample vessels of the reloaded sample rack.

4. The automatic analyzer according to claim 1, further comprising another analysis unit for analyzing a sample, wherein the buffer unit is arranged between the analysis unit and the another analysis unit.

5. The automatic analyzer according to claim 1, wherein the rack unloading position is outside of a path of a moving mechanism of the buffer unit.

6. The automatic analyzer according to claim 1, wherein the rack unloading position is a different position from the standby position.

7. The automatic analyzer according to claim 1, wherein the instruction means is further configured to record the comment from the input field for the sample vessel holding the sample instructed to unload and for all other sample vessels on the sample rack.

8. The automatic analyzer according to claim 7, wherein the instruction means is further configured to:
determine if the sample rack having the sample instructed to unload is in the buffer unit after recording the comment; and
when it is determined that the sample rack is in the buffer unit, controlling the buffer unit to move the sample rack to the rack unloading position.

9. The automatic analyzer according to claim 8, wherein:
the instruction means is further configured to move a reloaded sample rack from a rack loading position in the buffer unit when instructed to reload a sample in a sample vessel of the reloaded sample rack, and
the reloaded sample rack can be loaded from the rack loading position to an interior of the automatic analyzer without passing through the rack transport unit.

10. The automatic analyzer according to claim 9, wherein the buffer unit includes an ID reading section for identifying sample vessels of the reloaded sample rack, and the instruction means is further configured to:
control the ID reading section to read information from the sample vessels of the reloaded sample rack; and
determine if the sample vessels of the reloaded sample rack are the same as the sample vessels of the unloaded sample rack.

11. The automatic analyzer according to claim 10, wherein the instructions means is further configured to resume an analysis process that was stopped in order to unload the sample rack, when it is determined that the sample vessels of the reloaded sample rack are the same as the sample vessels of the unloaded sample rack.

12. The automatic analyzer according to claim 9, wherein the rack unloading position and the rack loading position are the same.

13. An automatic analyzer comprising:
an analysis unit for analyzing a sample;
a sample transport unit for transporting a sample vessel, which holds a sample, to the analysis unit;
a sample loading section for supplying the sample vessel to the sample transport unit;
a sample collecting section for collecting the sample vessel from the sample transport unit;
a buffer unit for holding the sample vessel in a standby position;
wherein the buffer unit is constructed such that the sample vessel can be transported from the standby position to the analysis unit without using the sample transport unit; and
an instruction means for controlling the automatic analyzer to unload the sample vessel, wherein the instruction means controls the automatic analyzer to move the sample vessel to a sample unloading position in the buffer unit when instructed to unload the sample in the sample vessel,
the sample vessel can be unloaded from the sample unloading position to an exterior of the automatic analyzer without passing through the sample transport unit,
the instruction means is configured to perform a search to determine if the sample instructed to unload is in the automatic analyzer, and
the instruction means is further configured to:
when it is determined that the sample instructed to unload is not in the automatic analyzer, display on a screen that the sample instructed to unload is not in the automatic analyzer, and when it is determined that the sample instructed to unload is in the automatic analyzer, display on the screen an input field for a comment.

14. The automatic analyzer according to claim 13, wherein the buffer unit is constructed such that the sample vessel unloaded from the automatic analyzer can be reloaded into the automatic analyzer at the sample disposing position so as to bypass said sample transport unit.

15. The automatic analyzer according to claim 14, wherein the buffer unit includes an ID reading section for identifying the reloaded sample vessel.

16. The automatic analyzer according to claim 13, further comprising another analysis unit for analyzing a sample, wherein the buffer unit is arranged between the analysis unit and the another analysis unit.

17. The automatic analyzer according to claim 13, wherein the sample unloading position is outside of a path of a moving mechanism of the buffer unit.

18. The automatic analyzer according to claim 13, wherein the sample unloading position is a different position from the standby position.

\* \* \* \* \*